United States Patent
Hopkins (10) Patent No.: US 9,138,229 B2
(45) Date of Patent: Sep. 22, 2015

(54) TISSUE RETAINING SYSTEM

(75) Inventor: Richard A. Hopkins, Kansas City, MO (US)

(73) Assignee: The Children's Mercy Hospital, Kansas City, MO (US)

( * ) Notice: Subject to any disclaimer, the term of this patent is extended or adjusted under 35 U.S.C. 154(b) by 865 days.

(21) Appl. No.: 12/481,294

(22) Filed: Jun. 9, 2009

(65) Prior Publication Data

US 2010/0042120 A1    Feb. 18, 2010

Related U.S. Application Data

(60) Provisional application No. 61/060,017, filed on Jun. 9, 2008.

(51) Int. Cl.
| | |
|---|---|
| *A61B 17/08* | (2006.01) |
| *A61B 17/11* | (2006.01) |
| *A61F 2/06* | (2013.01) |
| *C12M 3/00* | (2006.01) |
| *C12M 1/00* | (2006.01) |
| *A61B 17/04* | (2006.01) |

(52) U.S. Cl.
CPC ............... *A61B 17/11* (2013.01); *A61F 2/064* (2013.01); *C12M 21/08* (2013.01); *C12M 23/46* (2013.01); *C12M 29/10* (2013.01); *A61B 17/04* (2013.01); *A61B 2017/1107* (2013.01)

(58) Field of Classification Search
CPC .............. A61B 17/11; A61B 17/04; A61B 2017/1107; A61F 2/064; C12M 29/10; C12M 21/08; C12M 23/46
USPC ............... 73/807, 863.71, 866.4; 435/289.1; 600/36; 604/167.01, 174, 275; 606/108, 138–159
See application file for complete search history.

(56) References Cited

U.S. PATENT DOCUMENTS

| | | | | |
|---|---|---|---|---|
| 4,133,312 | A | * | 1/1979 | Burd ................................. 604/8 |
| 4,511,163 | A | * | 4/1985 | Harris et al. ............. 285/148.16 |
| 5,267,983 | A | * | 12/1993 | Oilschlager et al. .......... 604/533 |
| 6,030,395 | A | | 2/2000 | Nash |
| 6,234,188 | B1 | | 5/2001 | Moore, Jr. |
| 6,962,814 | B2 | | 11/2005 | Mitchell |
| 2003/0199083 | A1 | * | 10/2003 | Vilendrer et al. .......... 435/297.2 |
| 2005/0137614 | A1 | | 6/2005 | Porter |
| 2008/0132924 | A1 | | 6/2008 | McGuckin |

OTHER PUBLICATIONS

Seliktar et al., "Dynamic Mechanical Conditioning of Collagen-Gel Blood Vessel Constructs Induces Remodeling In Vitro," Annals of Biomedical Engineering, vol. 28, pp. 351-362 (2000).*

* cited by examiner

*Primary Examiner* — Michael Hobbs
(74) *Attorney, Agent, or Firm* — Tracey S. Truitt; Polsinelli PC (57) ABSTRACT

A tissue retaining system having a pair of tissue retainers for retaining two end portions of tubular tissue, such as a heart valve, to a bioreactor is disclosed. Each tissue retainer includes a stepped portion that permits custom fitting of the tissue retainer to a particular size of tubular tissue. The stepped portion of each tissue retainer defines a plurality of progressively larger concentric steps in which one of the concentric steps matches the size of a particular tubular tissue being engaged. The tubular tissue is then anchored to the tissue retainer by suture pull downs that anchor the tubular tissue to one of the concentric steps of the tissue retainer in a fluid tight engagement. This engagement process is repeated to secure the other end portion of the tubular tissue to another tissue retainer such that the tissue retaining system may then be engaged to the bioreactor.

15 Claims, 7 Drawing Sheets

TISSUE RETAINING SYSTEM

CROSS REFERENCE TO RELATED APPLICATIONS

This is a non-provisional patent application, which claims benefit of U.S. Provisional Application No. 61/060,017 filed on Jun. 9, 2008 and is herein incorporated by reference in its entirety.

FIELD

This document relates to a tissue retaining system, and in particular to a system and method of use for retaining hollow tubular tissue in a bioreactor.

BACKGROUND

Valve replacement is the most common surgical procedure in patients with structural heart disease. Approximately 87,000 valve replacement procedures were performed in the U.S. during the year 2000. Replacement valves commonly used in valve replacement procedures are typically either artificial valves or tissue valves made from animal tissues.

To avoid immunological rejection of valves made from animal tissues, tissue valves are commonly treated to crosslink collagen in order to mask the antigen sites of animal cells, thereby relying on the cartilaginous structural matrix of the heart valve. Recently, tissue engineering has been used to develop replacement tissue valves featuring a structural matrix seeded with cells harvested from a putative recipient for a valve transplant patient. The structural matrix may either be a decellularized donor valve, or an artificial matrix constructed of man-made materials.

Tissue-engineered heart valves are typically re-cellularized by seeding the heart valve structural matrix with cardiac myo-fibroblasts or multi-potential cells such as adult stem cells from bone marrow or circulating endothelial proginator cells to enhance the structural strength of the valve, followed by a seeding with endothelial cells in order to develop a thrombosis-resistant surface on the tissue valve. In order to provide the appropriate conditions for the attachment, growth, and proliferation of the seeded cells, a bioreactor is typically used. In the chamber of the bioreactor, living cells are contacted with the valve's structural matrix under conditions conducive to the adhesion of the fibroblasts and endothelial cells to the matrix. Because certain tissues, such as heart valves, may have end portions that provide little space for engagement to the bioreactor, it can be difficult to adequately secure the heart valve to the bioreactor, without damaging structural components of the semilunar valve mechanism (e.g., annula, leaflets, commissures, etc.). In addition, the difference in size between adult and children's heart valves requires a tissue retention system that can accommodate different size heart valves. Further, it is desirable that the heart valve be retained in the bioreactor in a non-destructive manner.

Therefore, a need in the art exists for an improved tissue retaining system and related method of use that overcomes the drawbacks of the prior art.

SUMMARY

In an embodiment, a tissue retainer for securing a tubular tissue may include a retainer body defining a distal opening in communication with a proximal opening through a conduit. The retainer body may define a stepped portion and a tubular portion. In particular, the stepped portion defines a plurality of concentric steps with each of the plurality of concentric steps including a vertical wall in communication with a horizontal wall, wherein the plurality of concentric steps provides a means of custom fitting the retainer body to a particular size of tubular tissue to be retained.

In one embodiment, a tissue retaining system for securing tubular tissue may include first and second tissue retainers with each of the first and second tissue retainers having a retainer body defining a distal opening in communication with a proximal opening through a conduit. The retainer body may define a stepped portion and a tubular portion. In particular, the stepped portion may define a plurality of progressively larger concentric steps adapted to engage different sizes of tubular tissue. The tubular tissue may include opposing end portions each having an external fibrous ridge with each end portion being adapted for engagement with either the first and second tissue retainers such that fluid flow communication is established between the first and second tissue retainers through the tubular tissue.

In another embodiment, a method for securing tubular tissue may include providing a tissue retainer having a retainer body defining a distal opening in communication with a proximal opening through a conduit. The retainer body may also include a stepped portion and a tubular portion. In particular, the stepped portion defines a plurality of progressively larger concentric steps with each respective concentric step including a vertical wall in communication with a horizontal wall. A tubular tissue having opposing end portions is then provided to custom fit the retainer body to the tubular tissue by matching one of the end portions of the tubular tissue to one of the plurality of progressively larger concentric steps. Once one of the end portions is matched with one of the plurality of concentric steps, the distal part of the stepped portion is cut off and a plurality of suture tie-downs may be established between one of the end portions of the tubular tissue and the flange of the retainer body. Finally, the end portions of the tubular tissue may be clamped to the stepped portion of the retainer body to provide a secure and fluid tight engagement.

In yet another embodiment, a retainer body may define a distal opening in communication with a proximal opening through an inner conduit defined by an inner wall. The retainer body may further define a conical portion in communication with a tapered portion with the conical portion having a generally tapered frustoconical shape, wherein the conical portion may provide a means for fitting the retainer body to a particular size of tubular tissue.

Additional objectives, advantages and novel features will be set forth in the description which follows or will become apparent to those skilled in the art upon examination of the drawings and detailed description which follows.

Corresponding reference characters indicate corresponding elements among the view of the drawings. The headings used in the figures should not be interpreted to limit the scope of the claims.

DETAILED DESCRIPTION

Figure 1:
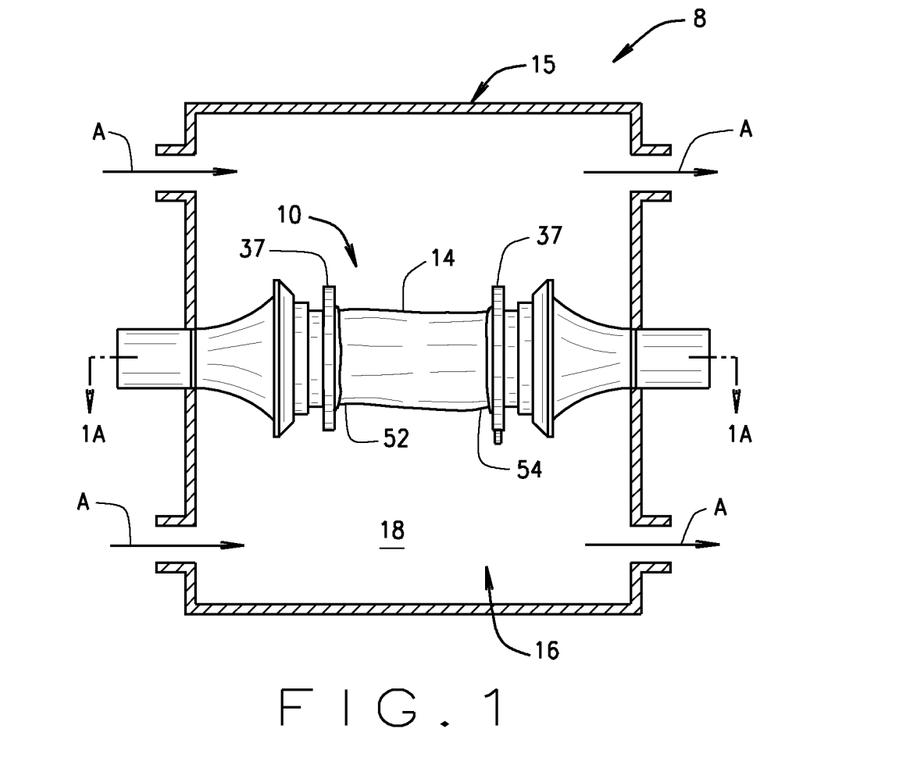
FIG. 1 is a simplified illustration of a bioreactor showing a tissue retaining system.
Figure 8A:
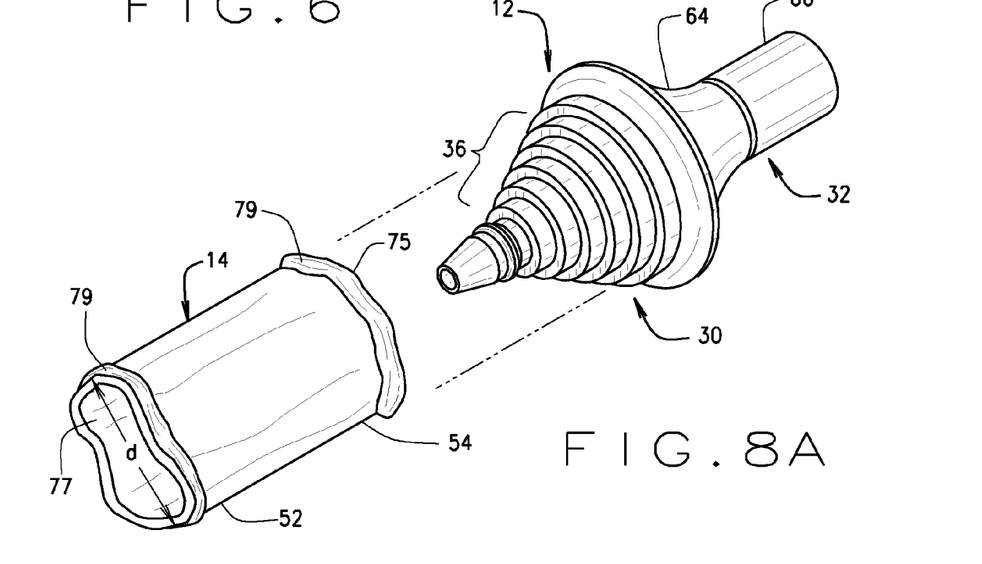
FIGS. 8A-8E illustrate the sequence of attaching a heart valve to the tissue retainer.

Referring to the drawings, an embodiment of the tissue retaining system is illustrated and generally indicated as 10 in FIG. 1. As shown in FIG. 1, the tissue retaining system 10 may be used for retaining a hollow tubular tissue 14, such as a heart valve, in a bioreactor 8 that provides nutrient media and mechanical stimuli to the tubular tissue 14. The bioreactor 8 includes a housing 15 that defines a bioreactor chamber 16 operatively associated with the tissue retaining system 10. In one embodiment, the tissue retaining system 10 may include first and second tissue retainers 12 that are attached to respective opposing first and second end portions 52, 54 of tubular tissue 14 with each respective first and second end portion 52, 54 having an external fibrous ridge 79 formed adjacent respective proximal and distal openings 75 and 77 (FIG. 8A).

Figure 1A:
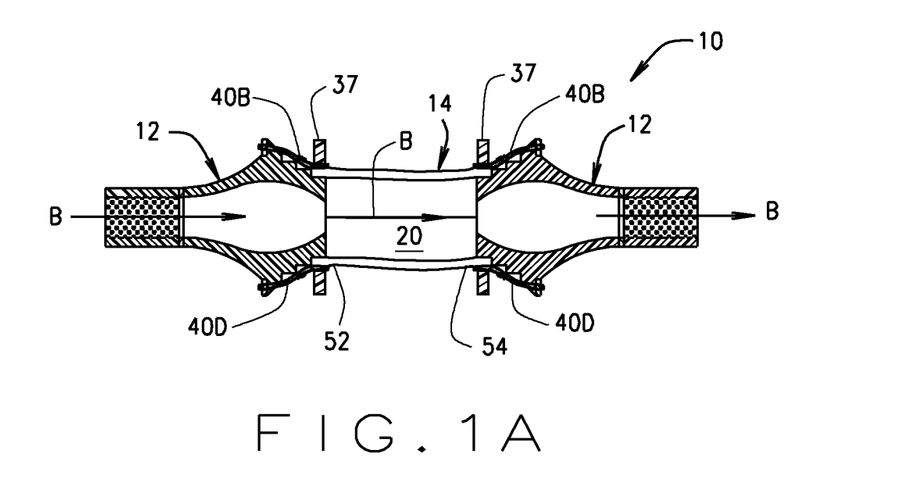
FIG. 1A is a simplified cross-sectional view of the tissue retaining system taken along line 1A-1A of FIG. 1.

Referring to FIGS. 1 and 1A, the housing 15 defines an exterior volume 18 adapted to receive a first fluid media that may flow along a fluid pathway A in the bioreactor 8. In addition, the hollow tubular tissue 14 retained within the bioreactor chamber 16 by the tissue retaining system 10 defines an interior volume 20 adapted to receive a second fluid media that may flow along a fluid pathway B between tissue retainers 12. The bioreactor 8 may include supply lines and pumps (not shown) that may independently control the speed and direction of movement of the fluid media within the exterior and interior volumes 18 and 20 of the bioreactor 8. In one aspect, fluid media may be stationary within exterior and/or interior volumes 18 and 20, fluid media may flow in one direction only through the exterior and interior volumes 18 and 20, or fluid media may flow in opposite directions through exterior and interior volumes 18 and 20. In all embodiments, the first and second fluid medias are segregated from one another when flowing through the exterior volume 18 of the housing 15 and the interior volume 20 of the tubular tissue 14, respectively.

In another aspect, the speed of the fluid flow within both the exterior volume 18 and the interior volume 20 may be uniform or varied through the bioreactor 8. For example, fluid flow speeds and directions within the exterior volume 18 and the interior volume 20 may be varied to mimic the dynamic flow conditions experienced by a heart valve or other tubular tissue 14 in vivo. The hydrostatic pressure within both the exterior and interior volumes 18 and 20 may also be independently controlled in a similar manner.

Figure 5A:
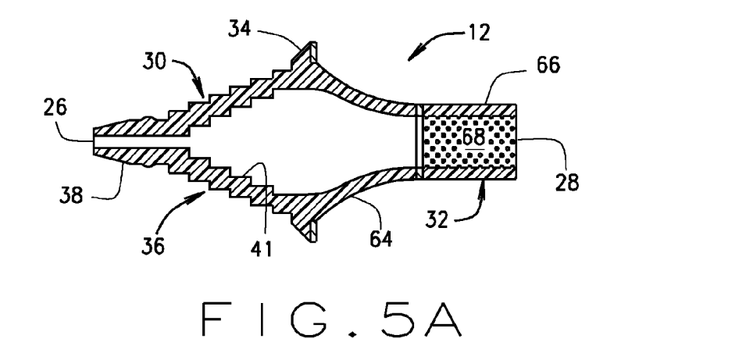
FIG. 5A is a cross-sectional view of another embodiment of the tissue retainer taken along line 5A-5A of FIG. 4.
Figure 6:
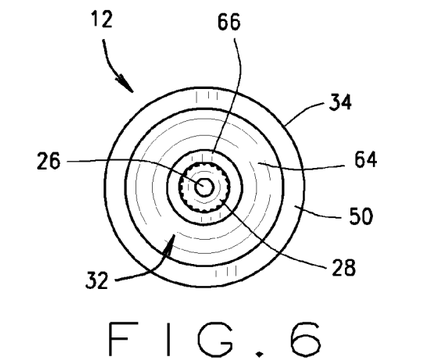
FIG. 6 is a top plan view of the tissue retainer shown in FIG. 2.
Figure 7:
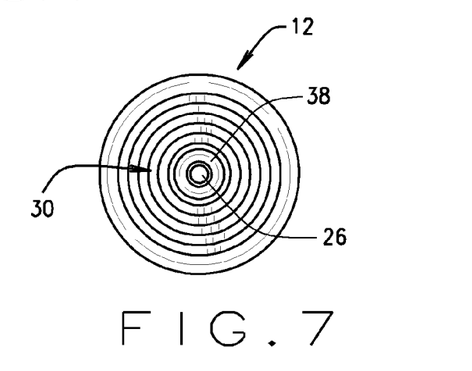
FIG. 7 is a bottom plan view of the tissue retainer shown in FIG. 2.

Referring to FIGS. 2-5, the tissue retainer 12 has a retainer body 22 that defines a distal tip 38 in communication with a distal opening 26 (FIG. 5A). The distal opening 26 is in fluid flow communication with an opposing proximal opening 28 through an inner conduit 24 defined by an inner wall 41 of the retainer body 22. The retainer body 22 further includes a stepped portion 30 in communication with a tubular portion 32 having a flange 34 interposed between portions 30 and 32.

The stepped portion 30 defines a plurality of progressively wider concentric steps 36 with each concentric step 36 defining a vertical wall 42 and a horizontal wall 44 that allow the tissue retainer 12 to be custom fit to accommodate any particular size of hollow tubular tissue 14 as shall be discussed in greater detail below. In one embodiment, the retainer body 22 may be made from a pliable and conformable material, such as medical-grade silicone; however, other plastic materials, such as polyurethane and polypropylene may be contemplated. In addition, the retainer body 22 may also be made from a metal and/or ceramics, or a composite of plastic, metal or ceramic materials.

In one embodiment, the tubular portion 32 may define a tapered part 64 joined to a tubular part 66 by a joining ring 48 using an adhesive, although other means for joining the ring to parts 64 and 66, such as various mechanical attachments, are contemplated. The joining ring 48 permits the tubular portion 32 to sufficiently flex when a force is applied to the retainer body 22. In the alternative, the tubular portion 32 may be of unitary construction with no joining ring 48 required to join the two parts 64 and 66. In another embodiment, the joining ring 48 may be made from any suitable metal or plastic material. As shown, the area of the inner wall 41 along the conduit 24 adjacent the proximal opening 28 of the tubular portion 32 defines a plurality of protrusions 68 that collectively provide a gripping surface when a tubular connector (not shown) of bioreactor 8 is inserted through the proximal opening 28 and into conduit 24 when engaging the tissue retaining system 10 to the bioreactor 8.

Figures 2, 3, 4, 5:
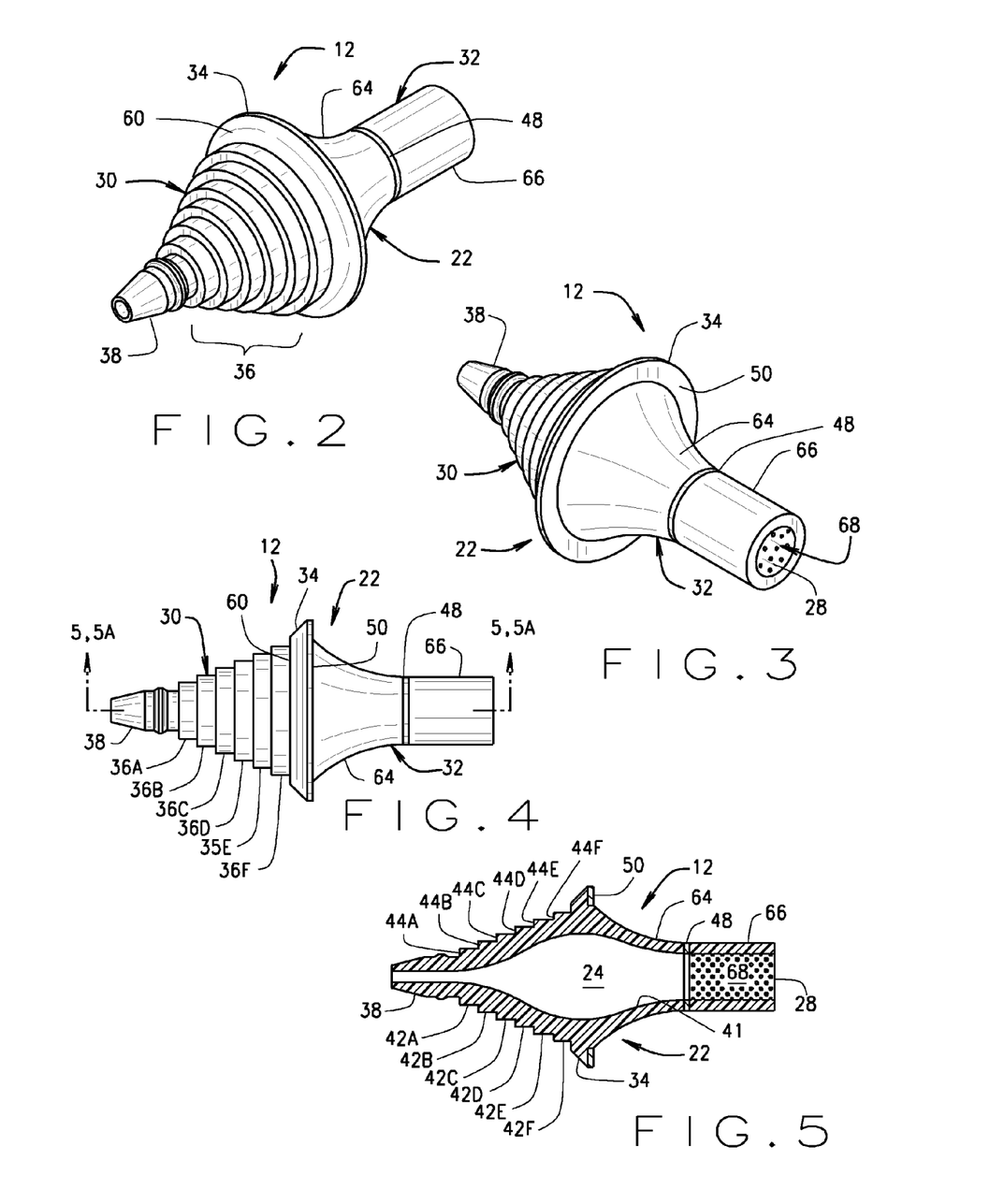
FIG. 2 is a front perspective view of an embodiment for a tissue retainer of the tissue retaining system.
FIG. 3 is a rear perspective view of the tissue retainer shown in FIG. 2.
FIG. 4 is a side view of a tissue retainer shown in FIG. 2.
FIG. 5 is a cross-sectional view of one embodiment of the tissue retainer taken along line 5-5 of FIG. 4.

Referring specifically to FIG. 3, the flange 34 may include a flange reinforcement ring 50 that provides structural support to flange 34. In one embodiment, the flange reinforcement ring 50 may be made from metal, although other hard materials, such as plastic, may also be used to form a thickened portion that structurally reinforces the flange 34. In other embodiments, the flange reinforcement ring 50 may be absent from the flange 34. In one embodiment, the flange 34 defines a beveled face 60 (FIG. 2) that provides a support surface when sizing an extremely large tubular tissue 14 that covers the entire stepped portion 30 of the retainer body 22. In addition, the beveled face 60 provides an engagement surface for securing the tubular tissue 14 to the retainer body 22 as shall be discussed in greater detail below.

As shown in FIG. 5, the conduit 24 defined by the inner wall 41 of retainer body 22 may have a tapered configuration that permits a generally constant wall thickness that ranges between 2 mm to 20 mm. In another embodiment illustrated in FIG. 5A, the inner wall 41 of the stepped portion 30 may define an inner concentric stepped pattern that conforms to the stepped pattern made by the plurality of concentric steps 36 in order to maintain a generally constant thickness of the inner wall 41.

Referring to FIGS. 4, 5 and 5A, as noted above an embodiment of the retainer body 22 may have a plurality of concentric steps 36 that include progressively widening concentric steps 36A, 36B, 36C, 36D, 36E and 36F to permit the user to size the tissue retainer 12 to fit the particular size of the tubular tissue 14 to be secured within the bioreactor 8. In addition, the distal tip 38 of the stepped portion 30 is sized to fit within the smallest size range of tubular tissue 14, such as semi-lunar or neonatal heart valves. However, other embodiments of the tissue retainer 12 may include more or less concentric steps 36 to fit a broader range of tubular tissue 14 sizes. As noted above, each concentric step 36 defines a horizontal wall 42 in communication with a vertical wall 44. The horizontal wall 42 is adapted to fit within the lumen of the tubular tissue 14 when the tissue is properly sized to the tissue retainer 12, while the vertical step 44 is adapted to abut the end portion 52, 54 of the tubular tissue 14 after it is fitted onto the proper concentric step 36 of the stepped portion 30. In this particular embodiment, concentric step 36A defines a horizontal step 42A and a vertical step 44A, while concentric steps 36B, 36C, 36D, 36E and 36F define respective horizontal walls 42B, 42C, 42D, 42E and 42F that communicate with respective vertical walls 44B, 44C, 44D, 44E and 44F.

Figure 9:
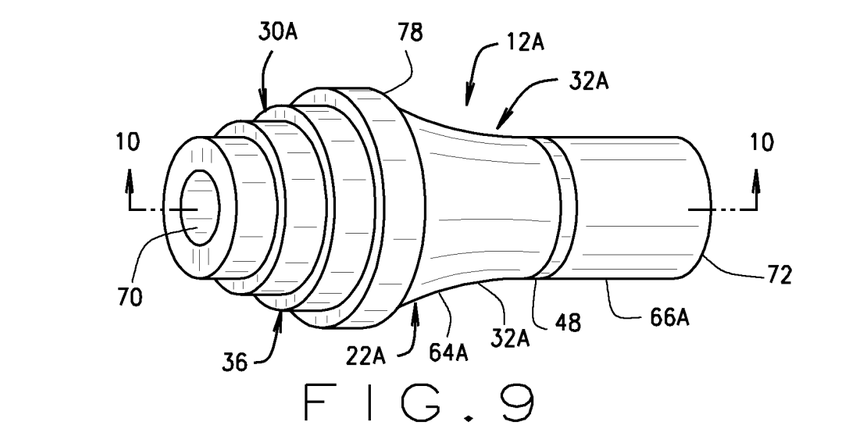
FIG. 9 is a front perspective view of one embodiment for the tissue retainer of the tissue retaining system.
Figure 10:
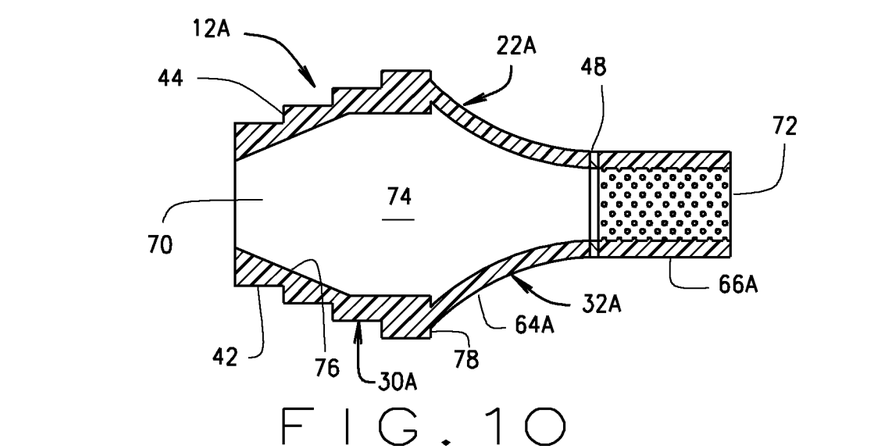
FIG. 10 is a cross-sectional view of the tissue retainer taken along line 10-10 of FIG. 9.

Referring to FIGS. 9 and 10, another embodiment of the tissue retainer, designated 12A, is illustrated. Tissue retainer 12A includes a retainer body 22A having a stepped portion 30A in communication with a tubular portion 32A having a flange 78 interposed between portions 30A and 32A. In addition, the retainer body 22A includes a distal opening 70 in communication with an opposing proximal opening 72 through an inner conduit 74 defined by an inner wall 76.

Similar to the other embodiments of the tissue retainer 12A stepped portion 30A also defines a plurality of progressively wider or larger concentric steps 36 with each concentric step 36 defining a vertical wall 42 and a horizontal wall 44 that allow the tissue retainer 12A to be custom fit to accommodate any particular size of hollow tubular tissue 14. The tubular portion 32A may define a tapered part 64A joined to a tubular part 66A by a joining ring 48 in the same manner as described above. The joining ring 48 serves the same purpose as other joining ring 48 for tissue retainer 12 which is to provide sufficient flex when an exterior force is applied to the retainer body 22A.

Referring specifically to FIG. 10, the inner wall 76 that defines the portion of the inner conduit 74 for the stepped portion 30A has a generally frustoconical configuration, while the portion of the inner conduit 74 for the tubular portion 32A has a gradually tapered configuration similar to the other embodiments of the tissue retainer 12A.

Figure 11:
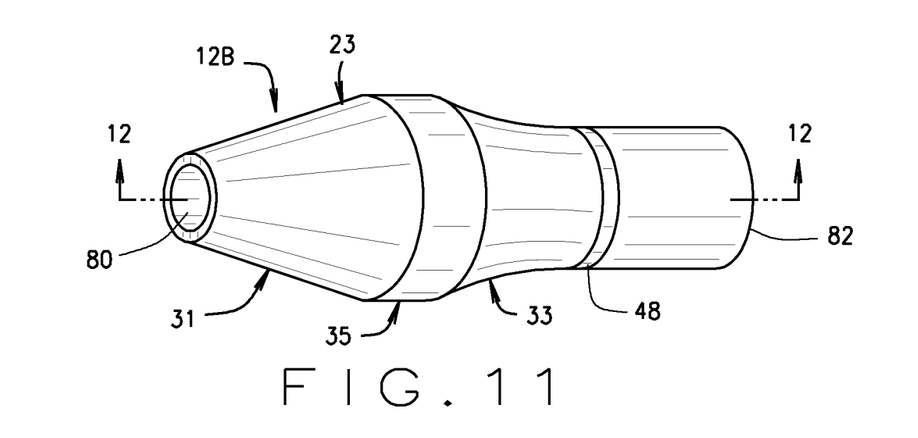
FIG. 11 is a front perspective view of another embodiment for the tissue retainer of the tissue retaining system.
Figure 12:
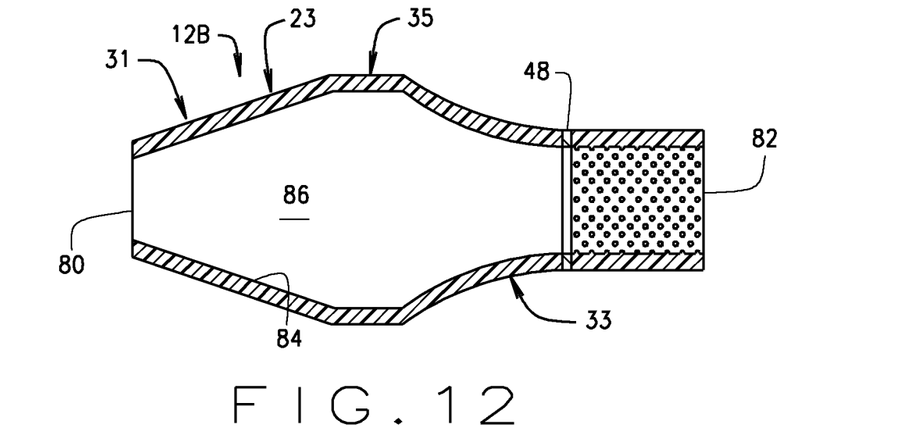
FIG. 12 is a cross-sectional view of the tissue retainer taken along line 12-12 of FIG. 11.

As shown in FIGS. 11 and 12, one embodiment of the tissue retainer, designated 12B, is illustrated. Tissue retainer 12B includes a retainer body 23 that defines a conical portion 31 and a tubular portion 33 with a rounded portion 35 formed between portions 31 and 33. Further, the retainer body 23 defines a distal opening 80 in communication with an opposing proximal opening 82 through an inner conduit 86 defined by an inner wall 84. Similar to the other embodiments, the tubular portion 33 may define a tapered part 67 joined to a tubular part 69 by a joining ring 48 that serves the same purpose as the other joining rings 48 discussed above.

Referring specifically to FIG. 12, the inner wall 84 that defines the portion of the inner conduit 86 for the conical portion 31 has a generally tapered conical configuration, while the portion of the inner conduit 86 for the tubular portion 33 has a gradually tapered configuration. In addition, the inner wall 84 may have a constant wall thickness throughout.

Figure 13:
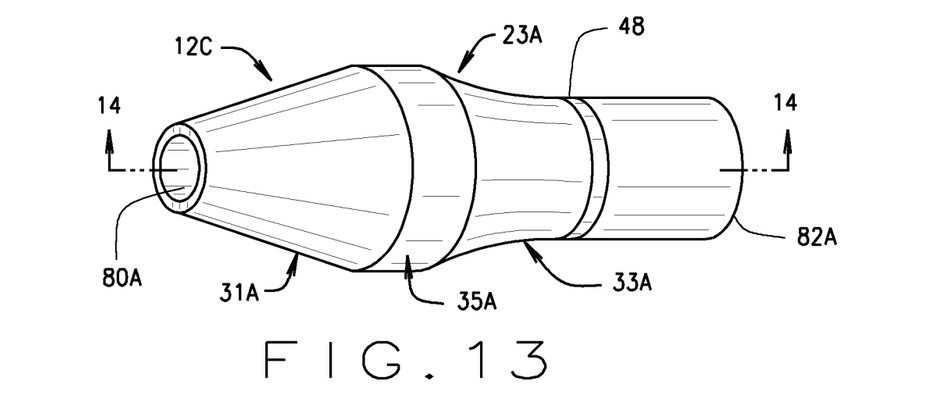
FIG. 13 is a front perspective view of yet another embodiment for the tissue retainer on the tissue retaining system.
Figure 14:
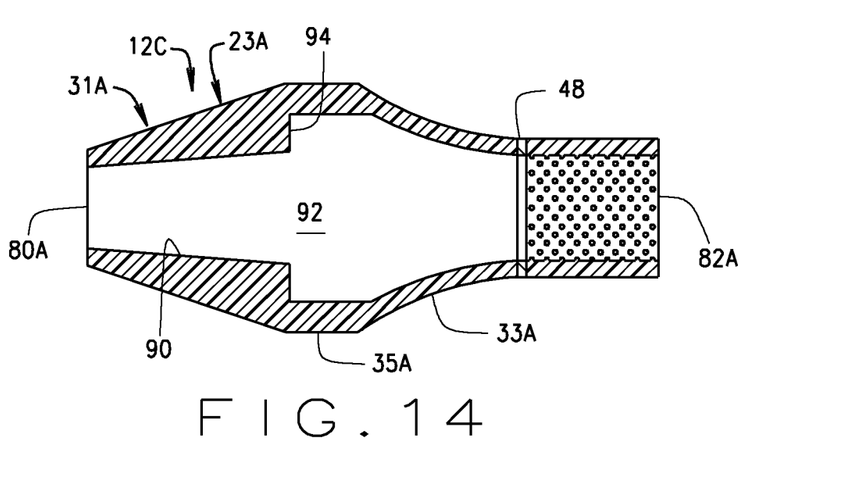
FIG. 14 is a cross-sectional view of the tissue retainer taken along line 13-13 of FIG. 13.

Referring to FIGS. 13 and 14, another embodiment of the tissue retainer, designated 12C, is illustrated. Tissue retainer 12C includes a retainer body 23A that defines a similarly shaped conical portion 31A and tubular portion 33A with a rounded portion 35A formed between portions 31A and 33A. In this embodiment, the rounded portion 35A may be shorter in length than rounded portion 35 of tissue retainer 12B, however other sizes of rounded portion 35A are contemplated. Further, the retainer body 23A defines a distal opening 80A in communication with an opposing proximal opening 82A through an inner conduit 92 defined by an inner wall 90. Similar to the other embodiments, the tubular portion 33A may define a tapered part 67A joined to a tubular part 69A by a joining ring 48 that serves the same purpose as the other joining rings 48 discussed above.

Referring specifically to FIG. 14, the inner wall 90 that defines the portion of the inner conduit 92 for the conical portion 31A has a gradually tapered conical configuration with a wall thickness that gradually thickens from the distal opening 80A, while the portion of the inner conduit 92 for the rounded portion 35A has a generally rounded configuration that forms a shoulder 94 with the conical portion 31A. The inner conduit 92 for the tubular portion 33A has a gradually tapered configuration similar to the other embodiments of tissue retainer 12C.

Referring back in FIGS. 1 and 5, the tissue retainer 12 is secured to the bioreactor 8 (FIG. 1) by inserting a tubular connector (not shown) through the proximal opening 28 and into the conduit 24 such that a friction fit is established between the tubular connector and the tissue retainer 12. As noted above, a plurality of protrusions 68 may be defined along a portion of the conduit 24 adjacent the proximal opening 28 for establishing a secure connection between the tissue retainer 12 and the tubular connector. In other embodiments, connections between the tissue retainer 12 and the bioreactor 8 (FIG. 10) may include mechanical connections to transmit forces and/or torques to the tissue, fluid connections to conduct cellular culture media or other fluids to the conduit 24, hydraulic connections to conduct hydrostatic or dynamic pressures to the tubular tissue 14, and combinations thereof.

Figure 8B:
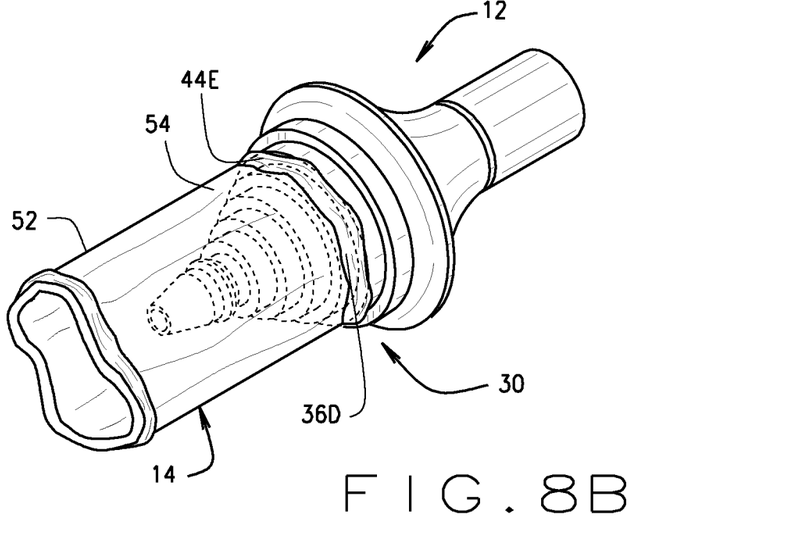

FIGS. 8A-8E illustrate the sequence of attaching the tubular tissue 14 to the tissue retaining system 10. As shown in FIG. 8A, the tubular tissue 14, such as a heart valve may be provided that has opposing end portions 52, 54 with end portion 52 defining a proximal opening 75 and end portion 54 defining a distal opening 77. In addition, a tissue retainer 12 having a stepped portion 30 defining a plurality of ever-widening concentric steps 36 may be provided to engage one end portion 52, 54 of tubular tissue 14 to a particular concentric step 36. End portion 52 or 54 is engaged such that the diameters "d" of either proximal or distal openings 75 and 77 substantially match the outer diameter of a particular concentric step 36 in order to properly size the retainer body 22 to fit the particular heart valve being secured to the tissue retainer 12. In one embodiment, distal opening 77 of tubular tissue 14 may fit around concentric step 36D such that tubular tissue 14 substantially contacts horizontal wall 42D and vertical wall 44E as shown in FIG. 8B.

Figure 8C:
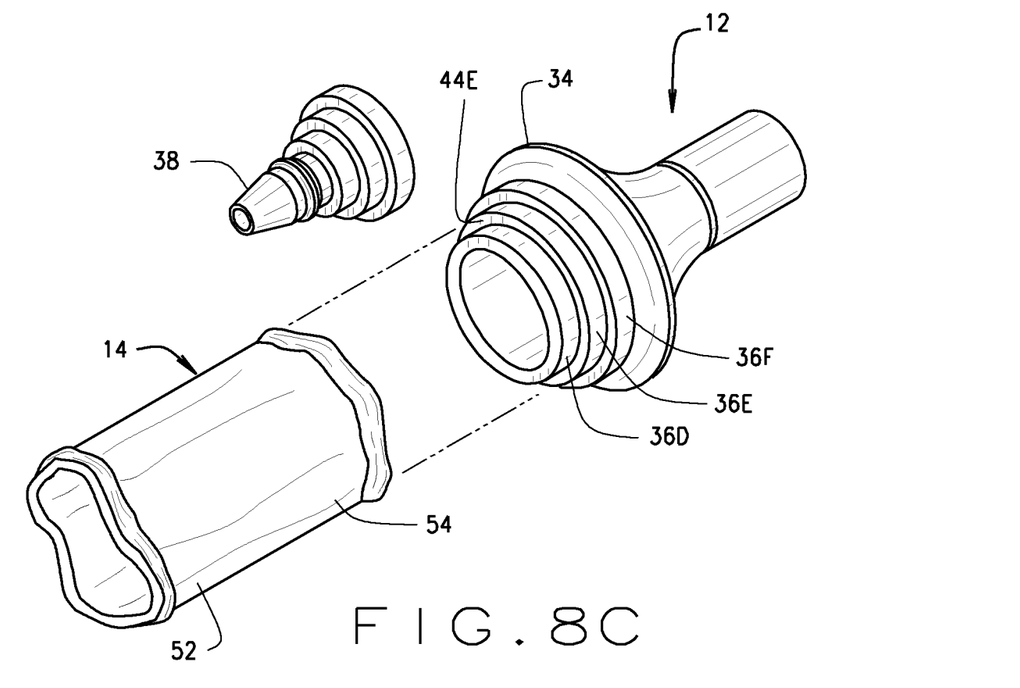
Figure 8D:
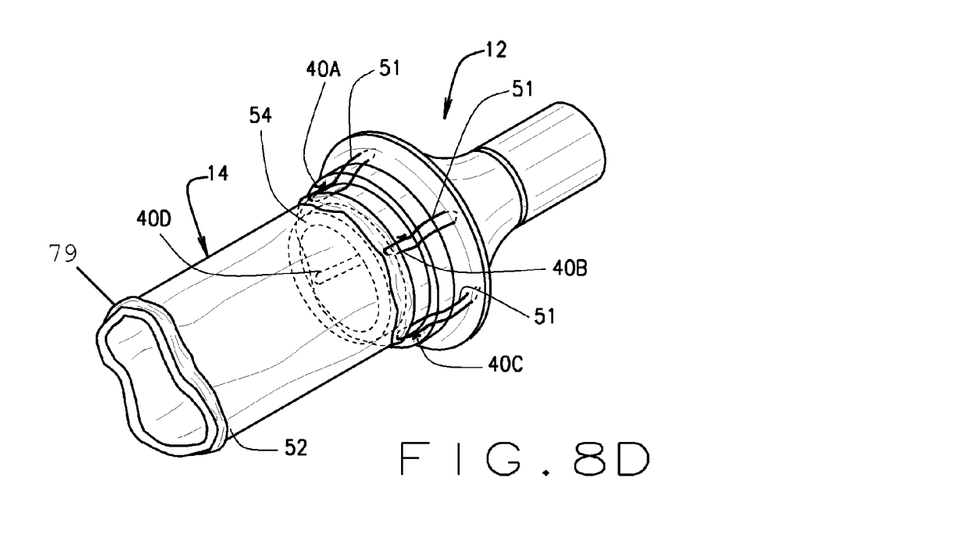

Once the user has properly sized the tubular tissue 14 to the tissue retainer 12, the user then cuts off and removes the distal part of the stepped portion 30 as shown in FIG. 8C such that the distal-most concentric step 36 is now concentric step 36D. After sizing of the tissue retainer 12 to match the particular tubular tissue 14, the user in one embodiment may establish one or more suture pull-downs between either any two steps 36, or the flange 34 and a step 36 to anchor and secure the tubular tissue 14 to the tissue retainer 12. As shown in FIG. 8D, the surgeon in one embodiment may suture the external fibrous ridge 79 of end portion 54 using a suture 51 along four equidistant suture points 40A-40D to the flange 34 of the tissue retainer 12 such that the suture does not penetrate into the lumen of the tubular tissue 14. Other embodiments may establish one or more other suture points 40 to anchor the tubular tissue 14 to the tissue retainer 12.

Figure 8E:
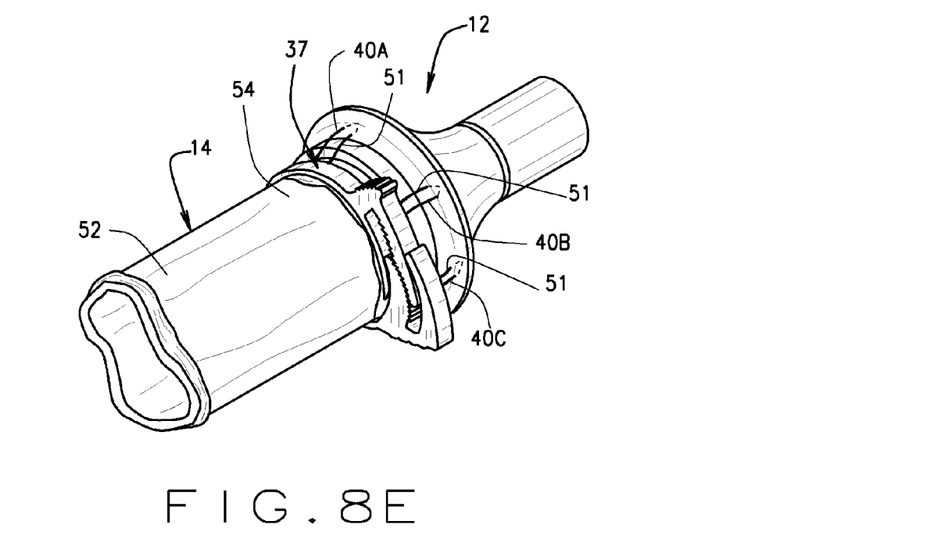

After the tubular tissue 14 has been tied down and anchored, the surgeon in one embodiment may engage a conventional clamp 37 to the tubular tissue 14 along the concentric step 36D to further secure the tubular tissue 14 to the tissue retainer 12 as shown in FIG. 8E. In this embodiment, the engagement of the clamp 37 establishes a fluid tight seal between the tubular tissue 14 and the concentric step 36D such that fluid media in exterior volume 18 of tubular tissue 14 remains segregated from the fluid media in interior volume 20 of the bioreactor chamber 16. In addition, the engagement of the clamp 37 will pull the suture pull-downs 40A-40D to tighten the connection between the tubular tissue 14 and tissue retainer 12. In other embodiments, the method may establish the suture pull-downs either before or after the clamp 37 has been secured the tubular tissue 14 to the tissue retainer 12.

Once the end portion 54 of tubular tissue 14 is secured to one tissue retainer 12, the other end portion 52 may be secured to another tissue retainer 12 in the same manner as described above so that both end portions 52 and 54 are secured to respective tissue retainers 12 as shown in FIG. 1A. After both end portions 52 and 54 are secured, the tubular portions 32 of each respective tissue retainer 12 are engaged to the tubular connectors of the bioreactor 8 as shown in FIG. 1 such that the tissue retaining system 10 is operatively associated with the bioreactor 8 and media fluid may flow through the interior volume 20 of the tubular tissue 14 and the exterior volume 18 of the bioreactor 8.

In an alternative embodiment, biocompatible glue (not shown) may be applied along the proximal and distal openings 75 and 77 of the tubular tissue 14 to further engage and secure the tubular tissue 14 to each of the tissue retainers 12. The use of the biocompatible glue may further ensure that a fluid tight seal is established between the exterior volume 18 of the bioreactor 8 and the interior volume 20 of the tubular tissue 14.

In one aspect, the tissue retainer 12 may be a single use, disposable device that is used once in the bioreactor 8 and then disposed of after use. In another aspect, the embodiment of the tissue retainer 12 having the stepped portion 30 may have a plurality of different sized embodiments with each stepped portion 30 having a particular size that does not require removal of the distal-most portions of the ever-widening concentric steps 36 when attempting to match the diameter of the proximal and distal openings 75 and 77 of the tubular tissue 14 to a particular size of tissue retainer 14. As such, the user may choose the proper size of tissue retainer 12 to match the particular size of tubular tissue 14 being engaged.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A tissue retainer for securing a tubular tissue comprising:
a retainer body defining a distal opening in communication with a proximal opening through an inner conduit defined by an inner wall with the retainer body further defining a stepped portion and a tubular portion, the stepped portion defining a plurality of adjacent concentric steps of increasing diameter in a direction from said distal opening to said proximal opening with each of the plurality of adjacent concentric steps including a vertical wall in direct communication with a horizontal wall wherein each concentric step is in direct communication to another concentric step and the concentric step closer to the distal end is preceding to the adjacent concentric step closer to the proximal end, wherein each said vertical wall extends from the horizontal wall of the preceding concentric step in a direction away from said inner conduit and wherein the plurality of concentric steps provides a means of fitting the retainer body to a particular size of tubular tissue, wherein said tissue retainer has one or more suture points.

2. The tissue retainer according to claim 1, further comprising a tubular tissue, wherein the means of fitting the retainer body to a particular size of said tubular tissue is accomplished by engaging said tubular tissue to an appropriate one of the plurality of concentric steps based on the particular size of said tubular tissue.

3. The tissue retainer according to claim 1, wherein each of the plurality of concentric steps is progressively larger.

4. The tissue retainer according to claim 1, wherein tubular portion includes a tapered part joined to a tubular part by a joining ring.

5. The tissue retainer according to claim1, wherein a flange is defined between the stepped portion and the tubular portion.

6. The tissue retainer according to claim1, wherein the inner wall has a constant thickness.

7. The tissue retainer according to claim 1, wherein the inner wall has a graduated thickness from the distal opening to the proximal opening.

8. The tissue retainer according to claim 1, further comprising a plurality of protrusions defined along the inner wall of the tubular portion adjacent the proximal opening.

9. The tissue retainer according to claim 1, further comprising a distal tip in communication with the distal opening.

10. A tissue retaining system comprising:
first and second tissue retainers, each of the first and second tissue retainers having a retainer body defining a distal opening in communication with a proximal opening through an inner conduit defined by an inner wall, each respective retainer body further defining a stepped portion and a tubular portion, the stepped portion defining a plurality of increasing diameter in a direction from said distal opening to said proximal opening with each of the plurality of adjacent concentric steps including a vertical wall in direct communication with a horizontal wall wherein each concentric step is in direct communication to another concentric step and the concentric step closer to the distal end is preceding to the adjacent concentric step closer to the proximal end, wherein each said vertical wall extends from the horizontal wall of the preceding concentric step in a direction away from said inner conduit and wherein the plurality of concentric steps provides a means of fitting the retainer body to a particular size of tubular tissue, wherein each said tissue retainer has one or more suture points;
tubular tissue having opposing proximal and distal end portions in communication with an interior volume, each of the proximal and distal end portion adapted for engagement with a respective first and second tissue retainers such that fluid flow communication is established between the inner conduit of first and second tissue retainers and the interior volume defined by the tubular tissue; and a housing engaged to the first and second tissue retainers, the housing defining an exterior volume that is segregated from the interior volume.

11. The tissue retaining system according to claim 10, further comprising a first fluid media for fluid flow through the interior volume and a second fluid media for separate fluid flow through the exterior volume of the housing.

12. The tissue retaining system according to claim 10, wherein the tubular portions of the first and second tissue retainers are engaged to the housing.

13. A method of securing tubular tissue comprising:
a) providing first and second tissue retainers, each of the first and second tissue retainers having a retainer body defining a distal opening in communication with a proximal opening through an inner conduit defined by an inner wall, each retainer body further defining a stepped portion and a tubular portion, the stepped portion defining a plurality of adjacent concentric steps of increasing diameter in a direction from said distal opening to said proximal opening with each of the plurality of adjacent concentric steps including a vertical wall in direct communication with a horizontal wall, wherein each concentric step is in direct communication to another concentric step and the concentric step closer to the distal end is preceding to the adjacent concentric step closer to the proximal end, wherein each said vertical wall extends from the horizontal wall of the preceding concentric step in a direction away from said inner conduit and wherein the plurality of concentric steps provides a means of fitting the retainer body to a particular size of tubular tissue, wherein each said tissue retainer has one or more suture points;
b) providing a tubular tissue having opposing end portions defining an interior volume with each of the opposing end portions having a respective diameter;
c) engaging each of the opposing end portions of the tubular tissue to one of the plurality of adjacent concentric steps for each respective first and second tissue retainers; and
d) establishing a plurality of suture tie-downs between each of the opposing end portions of the tubular tissue and the adjacent concentric steps of each retainer body for each of the first and second tissue retainers.

14. The method of securing tubular tissue according to claim 13, further comprising clamping the end portions of the tubular tissue to the stepped portion of each first and second tissue retainers with a clamp.

15. The method of securing tubular tissue of claim 13, further comprising removing prior to establishing the plurality of suture tie-downs any of the plurality of adjacent concentric steps of the stepped portion that fits within the interior volume of the tubular tissue when the tubular tissue is engaged to one of the adjacent concentric steps of the retainer body.

* * * * *